(12) United States Patent
Tokuda et al.

(10) Patent No.: US 12,011,254 B2
(45) Date of Patent: Jun. 18, 2024

(54) SYSTEM FOR AND METHOD OF TEMPERATURE-SENSITIVE FROZEN TISSUE IMAGING FOR CRYOABLATION MONITORING

(71) Applicant: The Brigham and Women's Hospital, Inc., Boston, MA (US)

(72) Inventors: Junichi Tokuda, Westwood, MA (US); Qun Wang, Beijing (CN); Kemal Tuncali, Newton, MA (US); Ravi Teja Seethamraju, Malden, MA (US); Clare M. Tempany, Charlestown, MA (US); Ehud J. Schmidt, Towson, MD (US)

(73) Assignee: The Brigham and Women's Hospital, Boston, MA (US)

( * ) Notice: Subject to any disclaimer, the term of this patent is extended or adjusted under 35 U.S.C. 154(b) by 8 days.

(21) Appl. No.: 16/951,074

(22) Filed: Nov. 18, 2020

(65) Prior Publication Data

US 2021/0153764 A1 May 27, 2021

Related U.S. Application Data

(60) Provisional application No. 62/939,238, filed on Nov. 22, 2019.

(51) Int. Cl.
| | |
|---|---|
| *A61B 5/055* | (2006.01) |
| *A61B 5/00* | (2006.01) |
| *A61B 5/06* | (2006.01) |
| *A61B 90/00* | (2016.01) |
| *G01R 33/50* | (2006.01) |
| *G01R 33/561* | (2006.01) |

(52) U.S. Cl.
CPC .............. *A61B 5/055* (2013.01); *A61B 5/06* (2013.01); *A61B 5/746* (2013.01); *A61B 90/37* (2016.02); *G01R 33/50* (2013.01); *G01R 33/5615* (2013.01)

(58) Field of Classification Search
CPC ............... G01R 33/4816; G01R 33/50; G01R 33/4804; G01R 33/5602; A61B 5/055; A61B 5/06; A61B 5/1075; A61B 2018/00577; A61B 2090/374; A61B 18/02; A61B 90/37
See application file for complete search history.

(56) References Cited

U.S. PATENT DOCUMENTS

| | | | | |
|---|---|---|---|---|
| 5,654,279 | A * | 8/1997 | Rubinsky | A61P 27/02 514/16.5 |
| 6,237,355 | B1 * | 5/2001 | Li | F25D 3/10 62/335 |
| 2021/0052314 | A1 * | 2/2021 | Holsing | A61B 34/10 |

OTHER PUBLICATIONS

Overduin, C. G., Fütterer, J. J., & Scheenen, T. W. (2016). 3D MR thermometry of frozen tissue: Feasibility and accuracy during cryoablation at 3T. Journal of Magnetic Resonance Imaging, 44(6), 1572-1579. (Year: 2016).*

(Continued)

*Primary Examiner* — Keith M Raymond
*Assistant Examiner* — Johnathan Maynard

(57) ABSTRACT

The present disclosure is directed to systems and methods for generating images using short tau inversion recovery, ultrashort echo time (STIR-UTE) MRI sequences. The STIR-UTE MRI sequences can be used to generate images that can differentiate between regions that are at temperatures that are either lethal or non-lethal to cell life. Thus, these sequences can be beneficial for implementations such as in monitoring cryoablation procedures.

16 Claims, 13 Drawing Sheets

(56) References Cited

OTHER PUBLICATIONS

Kobayashi, T., Monma, M., Baba, T., Ishimori, Y., Shiotani, S., Saitou, H., . . . & Homma, K. (2014). Optimization of inversion time for postmortem short-tau inversion recovery (STIR) MR imaging. Magnetic Resonance in Medical Sciences, 2013-0046. (Year: 2014).*

Tokuda, J., Tuncali, K., Seethamraju, R. T., Tempany, C. M., & Schmidt, E. J. Monitoring Cryoablation using Short Inversion Recovery Ultrashort Echo Time (STIR-UTE) MRI. International Society for Magnetic Resonance in Medicine. 2017 (Year: 2017).*

Dobak, J. (1998). A review of cryobiology and cryosurgery. Advances in Cryogenic Engineering, 889-896. (Year: 1998).*

Overduin, C. G., Jenniskens, S. F., Sedelaar, J. M., Bomers, J. G., & Fütterer, J. J. (2017). Percutaneous MR-guided focal cryoablation for recurrent prostate cancer following radiation therapy: retrospective analysis of iceball margins and outcomes. European radiology, 27, 4828-4836. (Year: 2017).*

Siegel, Rebecca L., Kimberly D. Miller, and Ahmedin Jemal. "Cancer statistics, 2019." CA: a cancer journal for clinicians 69.1 (2019): 7-34.

Roy, S., et al. "Active treatment in low-risk prostate cancer: a population-based study." Current Oncology 26.4 (2019): e535-e540.

Gandaglia, Giorgio, et al. "Structured population-based prostate-specific antigen screening for prostate cancer: the European Association of Urology position in 2019." European urology 76.2 (2019): 142-150.

Ilic, Dragan, et al. "Prostate cancer screening with prostate-specific antigen (PSA) test: a systematic review and meta- analysis." bmj 362 (2018): k3519.

Fenton, Joshua J., et al. "Prostate-specific antigen-based screening for prostate cancer: evidence report and systematic review for the US Preventive Services Task Force." Jama 319.18 (2018): 1914-1931.

Shen, Xinglei, and Parvesh Kumar. "Trade-off between treatment of early prostate cancer and incidence of advanced prostate cancer in the prostate screening era." The Journal of Urology 195.5 (2016): 1397-1402.

Shah, Taimur T., et al. "Early-medium-term outcomes of primary focal cryotherapy to treat nonmetastatic clinically significant prostate cancer from a prospective multicentre registry." European urology 76.1 (2019): 98-105.

Edison, Eric, Taimur Tariq Shah, and Hashim U. Ahmed. "Focal ablation of early-stage prostate cancer: candidate selection, treatment guidance, and assessment of outcome." Urologic Clinics 44.4 (2017): 575-585.

Valerio, Massimo, et al. "New and established technology in focal ablation of the prostate: a systematic review." European urology 71.1 (2017): 17-34.

Ganzer, Roman, et al. "Which technology to select for primary focal treatment of prostate cancer ?—European Section of Urotechnology (ESUT) position statement." Prostate cancer and prostatic diseases 21.2 (2018): 175-186.

Demirel, Cihan H., Muammer Altok, and John W. Davis. "Focal therapy for localized prostate cancer: is there a "middle ground" between active surveillance and definitive treatment?." Asian journal of andrology 21.1 (2019): 37.

Golbari, Nicole M., and Aaron E. Katz. "Salvage therapy options for local prostate cancer recurrence after primary radiotherapy: a literature review." Current urology reports 18.8 (2017): 63.

Schmid, F. A., et al. "Prospective multicentre study using high intensity focused ultrasound (HIFU) for the focal treatment of prostate cancer: safety outcomes and complications." Urologic Oncology: Seminars and Original Investigations. vol. 38. No. 4. Elsevier, 2020.

Johnston, Maximilian J., et al. "Focal high-intensity Focussed ultrasound partial gland ablation for the treatment of localised prostate cancer: a report of medium-term outcomes from a single-center in the United Kingdom." Urology 133 (2019): 175-181.

Tourinho-Barbosa, Rafael R., et al. "Focal therapy for localized prostate cancer with either high intensity focused ultrasound or cryoablation: a single institution experience." The Journal of Urology 203.2 (2020): 320-330.

van Luijtelaar, Annemarijke, et al. "Focal laser ablation as clinical treatment of prostate cancer: report from a Delphi consensus project." World journal of urology 37.10 (2019): 2147-2153.

Walser, Eric, et al. "Focal laser ablation of prostate cancer: results in 120 patients with low-to intermediate-risk disease." Journal of Vascular and Interventional Radiology 30.3 (2019): 401-409.

Knull, Eric, et al. "Evaluation of tumor coverage after MR-guided prostate focal laser ablation therapy." Medical Physics 46.2 (2019): 800-810.

Chao, Brian, Elton Llukani, and Herbert Lepor. "Two-year outcomes following focal laser ablation of localized prostate cancer." European Urology Oncology 1.2 (2018): 129-133.

Ahrar, Kamran, et al. "Real-time MRI-guided cryoablation of small renal tumors at 1.5 T." Investigative radiology 48.6 (2013): 437.

Klossner, Daniel P., et al. "Cryosurgical technique: assessment of the fundamental variables using human prostate cancer model systems." Cryobiology 55.3 (2007): 189-199.

Daniel, Bruce L., Kim Butts, and Walter F. Block. "Magnetic resonance imaging of frozen tissues: Temperature-dependent MR signal characteristics and relevance for MR monitoring of cryosurgery." Magnetic Resonance in Medicine: An Official Journal of the International Society for Magnetic Resonance in Medicine 41.3 (1999): 627-630.

Butts, Kim, et al. "Temperature quantitation and mapping of frozen tissue." Journal of Magnetic Resonance Imaging 13.1 (2001): 99-104.

Wansapura, Janaka P., et al. "In Vivo MR Thermometry of Frozen Tissue Using $R2^*$ and Signal Intensity1." Academic radiology 12.9 (2005): 1080-1084.

Overduin, Christiaan G., Jurgen J. Futterer, and Tom WJ Scheenen. "3D Mr thermometry of frozen tissue: Feasibility and accuracy during cryoablation at 3T." Journal of Magnetic Resonance Imaging 44.6 (2016): 1572-1579.

Grodzki, David M., Peter M. Jakob, and Bjoern Heismann. "Ultrashort echo time imaging using pointwise encoding time reduction with radial acquisition (PETRA)." Magnetic resonance in medicine 67.2 (2012): 510-518.

Fung, B. M. "Non-freezable water and spin-lattice relaxation time in muscle containing a growing tumor." Biochimica et Biophysica Acta (BBA)-General Subjects 362.1 (1974): 209-214.

Fung, B. M., and Tim W. McGaughy. "The state of water in muscle as studied by pulsed NMR." Biochimica et Biophysica Acta (BBA)-General Subjects 343.3 (1974): 663-673.

Carl, Michael, Graeme M. Bydder, and Jiang Du. "UTE imaging with simultaneous water and fat signal suppression using a time-efficient multispoke inversion recovery pulse sequence." Magnetic resonance in medicine 76.2 (2016): 577-582.

Captur, Gabriella, et al. "A medical device-grade T1 and ECV phantom for global T1 mapping quality assurance—the T 1 Mapping and ECV Standardization in cardiovascular magnetic resonance (T1MES) program." Journal of cardiovascular magnetic resonance 18.1 (2016): 58.

Fedorov, Andriy, et al. "3D Slicer as an image computing platform for the Quantitative Imaging Network." Magnetic resonance imaging 30.9 (2012): 1323-1341.

Hsu, Shu-Hui, et al. "Quantitative characterizations of ultrashort echo (UTE) images for supporting air-bone separation In the head." Physics in Medicine & Biology 60.7 (2015): 2869.

Tustison, Nicholas J., et al. "N4ITK: improved N3 bias correction." IEEE transactions on medical imaging 29.6 (2010): 1310-1320.

Seifert, Joachim K., et al. "A pig model of hepatic cryotherapy. In vivo temperature distribution during freezing and histopathological changes." Cryobiology 47.3 (2003): 214-226.

Fung, B. M., Dana L. Durham, and David A. Wassil. "The state of water in biological systems as studied by proton and deuterium relaxation." Biochimica et Biophysica Acta (BBA)-General Subjects 399.1 (1975): 191-202.

Kaye, Elena A., et al. "Consistency of signal intensity and $T2^*$ in frozen ex vivo heart muscle, kidney, and liver tissue." Journal of

(56) References Cited

OTHER PUBLICATIONS

Magnetic Resonance Imaging: An Official Journal of the International Society for Magnetic Resonance in Medicine 31.3 (2010): 719-724.

Lustig, Michael, and John M. Pauly. "SPIRIT: iterative self-consistent parallel imaging reconstruction from arbitrary k-space." Magnetic resonance in medicine 64.2 (2010): 457-471.

Qian, Yongxian, and Fernando E. Boada. "Acquisition-weighted stack of spirals for fast high-resolution three-dimensional ultra-short echo time MR imaging." Magnetic Resonance in Medicine: An Official Journal of the International Society for Magnetic Resonance in Medicine 60.1 (2008): 135-145.

\* cited by examiner

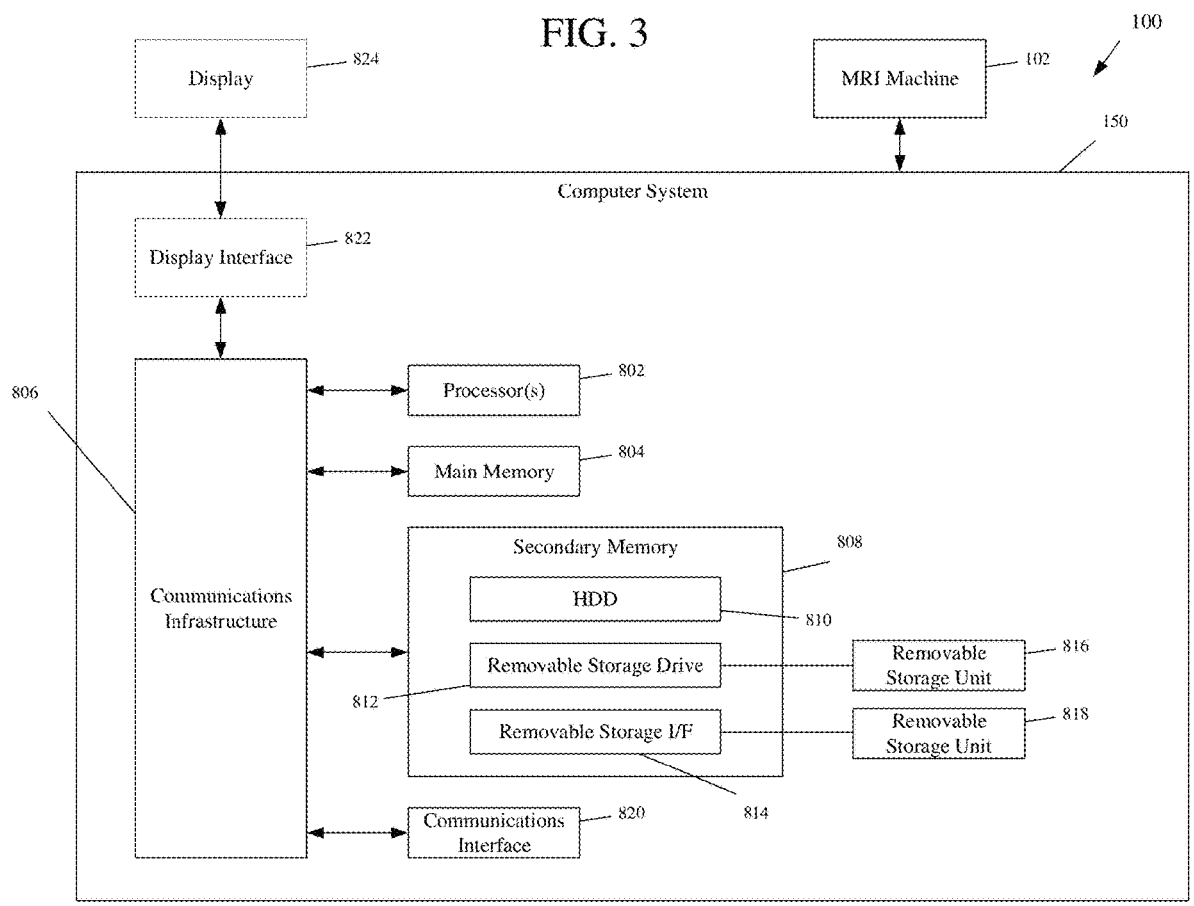

FIG. 4A
FIG. 4B
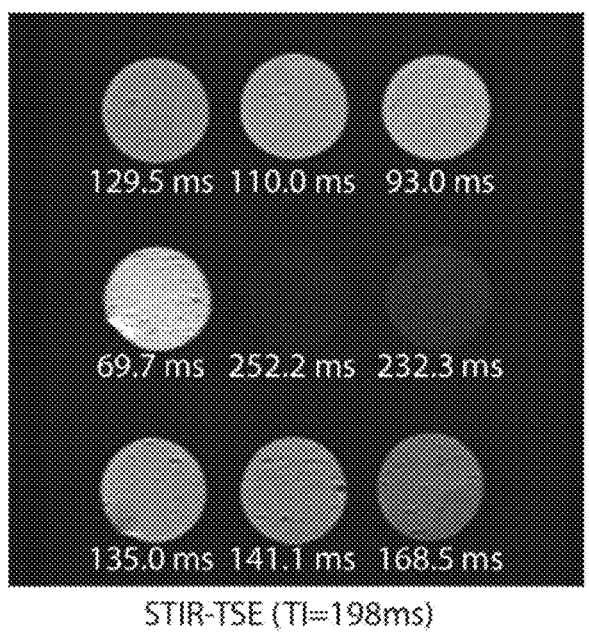
STIR-TSE (TI=198ms)
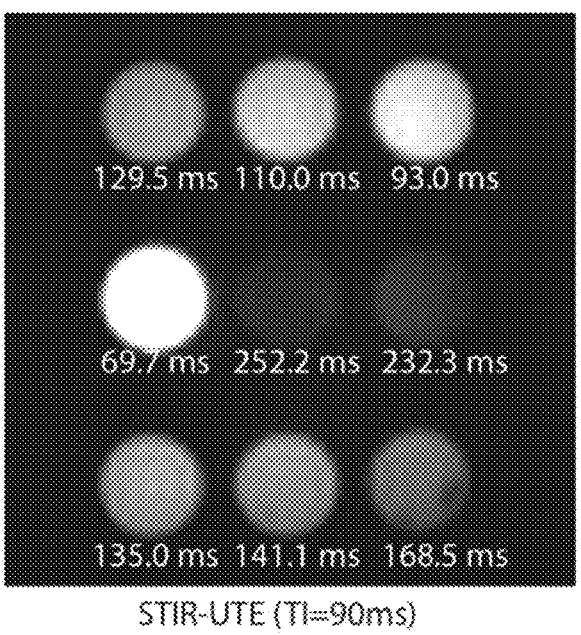
STIR-UTE (TI=90ms)

SYSTEM FOR AND METHOD OF TEMPERATURE-SENSITIVE FROZEN TISSUE IMAGING FOR CRYOABLATION MONITORING

PRIORITY

The present application claims priority to U.S. Provisional Patent Application No. 62/939,238, titled "SYSTEM FOR AND METHOD OF TEMPERATURE-SENSITIVE FROZEN TISSUE IMAGING FOR CRYOABLATION MONITORING," filed Nov. 22, 2019, which is hereby incorporated by reference herein in its entirety.

This invention was made with government support under grant number EB015898 awarded by the National Institutes of Health. The government has certain rights in the invention.

BACKGROUND

Cryoablation is a medical technique whereby extreme cold is used to destroy tissue. Cryoablation can be used to treat a variety of different conditions, including cancer (e.g., prostate or kidney cancer) and arrhythmia. Commonly, cryoablation is performed by inserting hollow needles (cryoprobes) into a target tissue (e.g., a tumor) and then circulating cooled, thermally conductive, fluids through the cryoprobes, which cools the tips of the cryoprobes and the surrounding tissue in context with the tips. However, other techniques can alternatively be used to cool the cryoprobes, such as using gases that have large enthalpy changes during expansion. The extreme cold destroys the tissue by forming ice crystals, interrupting blood flow, and/or inducing apoptosis.

Generally, an imaging modality is used to monitor cryotherapy ablation procedures in order to ensure that the individual cryoprobes are positioned correctly and that the target tissue is being cooled to destroy the tissue in the desired manner (i.e., to avoid too little or too much tissue from being destroyed). Magnetic resonance imaging (MRI) is an attractive tool for monitoring cryoablation procedures because MRI shows the strongest contrast at freezing temperatures relative to other imaging modalities. Thus, MRI can provide real-time cryothermometry. In particular, intraprocedural MRI is known to provide excellent visualization of tumors and also visualizes the volume frozen to a temperature that is below 0° C. (referred as the "ice ball"), which makes it an attractive tool for cryoablation monitoring. However, there are still drawbacks associated with conventional MRI monitoring techniques for cryoablation procedures. For example, conventional MRI sequences, which use echo times greater than 500 msec, display all tissues below 0° C. as dark. However, studies have shown that temperatures in the range of −20° C. to −40° C. are required to achieve total necrosis in cancerous tissues. Because any area below 0° C. is displayed as dark, but cell death is not induced until the tissue reaches lower temperatures, the entire visualized "dark" region may not be at a sufficient lethal temperature and may overestimate the actual ablated zone. In other words, the "ice ball" region visualized using conventional MRI techniques is not coextensive with the region of the tissue that is at a lethal temperature. Therefore, the physician cannot depend on the visualized size and volume of the ice ball to determine the correct tumor coverage and adequate treatment margins. In particular, conventional MRI spin-lattice relaxation time ($T_1$-) or spin-spin relaxation time ($T_2$-) weighted sequences which have a time-to-echo (TE)>1 ms both show the entire ice ball as a signal void due to the short spin dephasing ($T_2^*$) relaxation time of tissues below 0° C., where $T_2^* \ll 1$ ms. Since cell death is commonly understood to occur at approximately −40° C. and below, this means that one cannot use MRI to delineate between tissue that has been sufficiently cooled to induce cell death and other tissue that is below 0° C., but has not been cooled to a lethal temperature. Therefore, physicians are forced to estimate the volume of tissue that is at the lethal temperature from the visualized volume of "dark" region of tissue during the procedure. Such estimations are inherently imprecise, often resulting in either healthy tissue from being improperly ablated or the target region (e.g., a tumor) from not being ablated to the necessary extent. The extent of cell death in the target tissue can be post-procedurally assessed by waiting for the target tissue to thaw and then reimaging the patient. However, because it can take extended periods of time for the tissue to thaw (e.g., hours), this is seldom actually done in practice.

As one attempt to solve these problems, MR thermometry of frozen tissue using ultrashort echo time (UTE) MRI sequences was proposed. Those techniques estimate temperature based on quantifying the tissue $T_2^*$, which is temperature dependent, or using the normalized UTE signal intensity, which is proportional to $T_2^*$. However, these techniques are not practical to perform in clinical applications because they require calculations of $T_2^*$ based on multiple images that are obtained at different TEs and the signal changes for the different TEs are so minute that it can be hard to differentiate the signal decay. Also, these calculations are difficult to perform when imaging in regions that are susceptible to physiological motion, making these techniques very difficult to implement clinically.

Accordingly, there is a need in the technical field for an MRI technique that is specifically adapted to differentiate between tissue at lethal and non-lethal temperatures so that medical personnel can accurately visualize and measure the volume of the ablated tissue during a cryoablation procedure and ensure full coverage of the focal tumor.

SUMMARY

In one embodiment, the present disclosure is directed to systems and methods for generating images using a short tau inversion recovery UTE (STIR-UTE) MRI sequence. STIR-UTE MRI images with specifically selected inversion-times, as determined by the $T_1$ of frozen tissue at the corresponding magnetic field strength, show regions approximately between −40° C. and −8° C. as hyperintense, with tissues at lower and higher temperatures appearing dark. Accordingly, a STIR-UTE MRI sequence is particularly adapted for implementations such as in monitoring cryoablation procedures because it allows for the visualization and, thus, identification of the region likely to be above the cell death temperature inside the frozen tissue.

In one embodiment, an MRI system for imaging a patient, the MRI system comprising: an MRI machine; and a computer system coupled to the MRI machine, the computer system comprising: a processor, and a memory coupled to the processor, the memory storing instructions that, when executed by the processor, cause the computer system to: control the MRI machine to apply an MRI sequence comprising a short tau inversion recovery sequence and an ultrashort echo time, wherein the short tau inversion recovery sequence is directed to an upper temperature corresponding to a first $T_1$ value and a lower temperature corresponding to a second $T_1$ value, and reconstruct an image of the patient in response to the MRI sequence, the image visualizing a region corresponding to the upper temperature and the lower temperature.

In one embodiment, a method for imaging a patient, the method comprising: controlling, via a computer system, an MRI machine to apply an MRI sequence comprising a short tau inversion recovery sequence and an ultrashort echo time, wherein the short tau inversion recovery sequence is directed to an upper temperature corresponding to a first $T_1$ value and a lower temperature corresponding to a second $T_1$ value; and reconstructing, via the computer system, an image of the patient in response to the MRI sequence, the image visualizing a region corresponding to the upper temperature and the lower temperature.

In one embodiment, a method for monitoring a patient during a cryoablation procedure, the method comprising: visualizing, via an MRI system configured to apply an MRI sequence comprising a short tau inversion recovery sequence and an ultrashort echo time, wherein the short tau inversion recovery sequence is directed to an upper temperature corresponding to a first $T_1$ value and a lower temperature corresponding to a second $T_1$ value, a lethal region relative to a target region corresponding to the upper temperature and the lower temperature during the cryoablation procedure; determining whether the visualized lethal region is coextensive with the target region; and providing feedback for the cryoablation procedure according to the determination.

FIGURES

The accompanying drawings, which are incorporated in and form a part of the specification, illustrate the embodiments of the invention and together with the written description serve to explain the principles, characteristics, and features of the invention. In the drawings:

FIG. 3 is a diagram of a computer system architecture, in accordance with at least one aspect of the present disclosure.

FIG. 4A is a set of images of phantoms obtained using a conventional $T_2$-weighted turbo spin echo (TSE) MRI sequence, in accordance with at least one aspect of the present disclosure.

FIG. 4B is a set of images of phantoms obtained using a STIR-UTE MRI sequence, in accordance with at least one aspect of the present disclosure.

DESCRIPTION

This disclosure is not limited to the particular systems, devices and methods described, as these may vary. The terminology used in the description is for the purpose of describing the particular versions or embodiments only, and is not intended to limit the scope.

Methods and Systems for STIR-UTE MRI Monitoring

This disclosure is generally directed to MRI sequences and MRI systems configured to utilize such sequences. An MRI sequence can generally be defined as a series of radiofrequency (RF) pulses and gradients that are used to generate a set of images having a particular desired appearance. Various aspects of the disclosure utilize inversion recovery pulse sequences, which are a type of MRI sequence that is used to selectively zero or null the signal for certain types of tissues (e.g., fat or fluid). In various embodiments, MRI systems can be programmed or otherwise configured to implement these types of sequences for imaging a subject.

Figure 1:
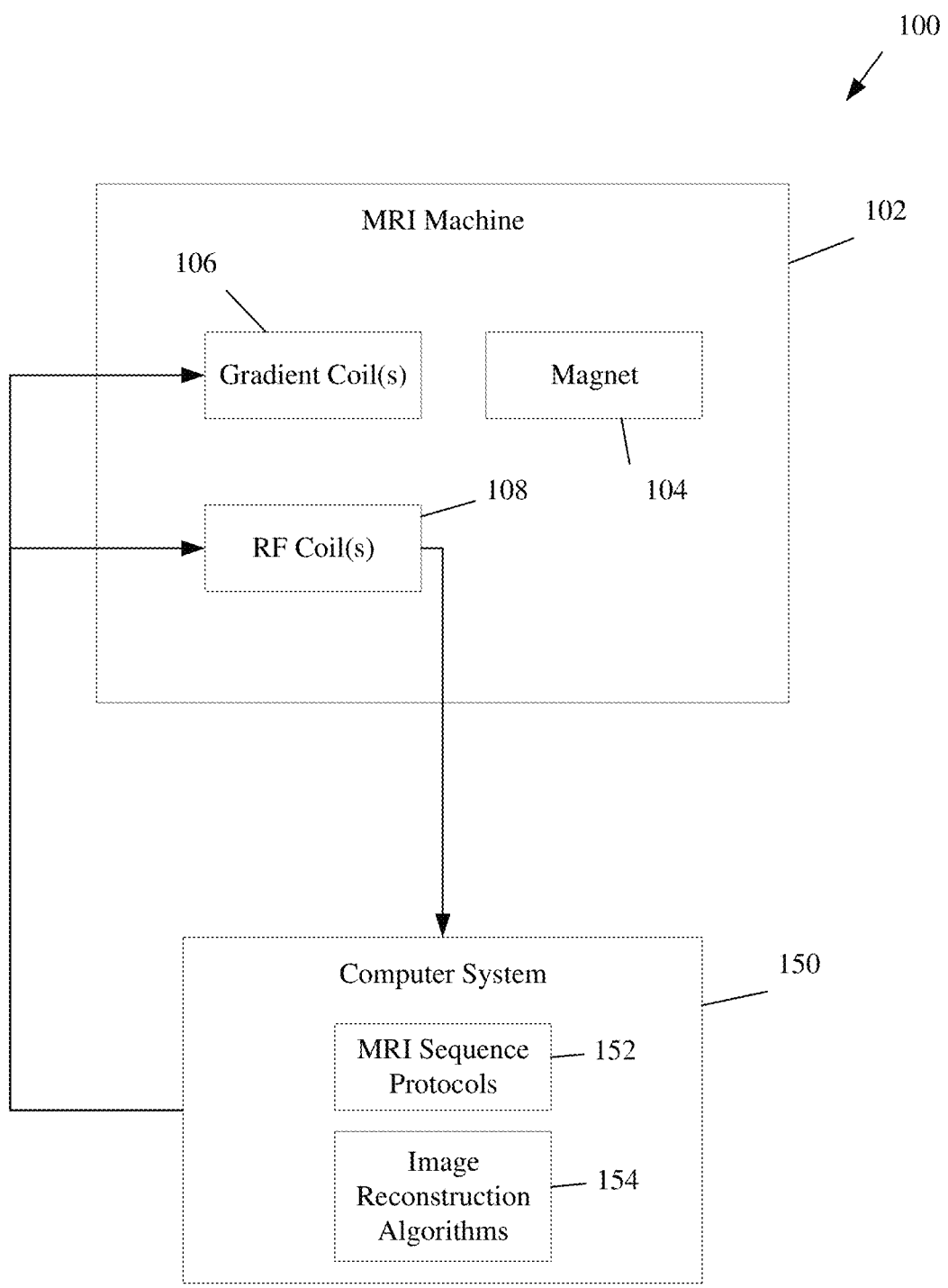
FIG. 1 is a diagram of an MRI system configured to implement a STIR-UTE MRI sequence, in accordance with at least one aspect of the present disclosure.

Referring now to FIG. 1, there is shown a diagram of an illustrative MRI system 100 that can be used in various embodiments of the present disclosure. The MRI system 100 can include an MRI machine 102 that is operably coupled to a computer system 150. The MRI machine 102 can include a magnet 104 extending along a bore that is configured to receive a patient therein and that is configured to produce a generally uniform magnetic field, one or more gradient coils 106 that are configured to produce magnetic field gradients (e.g., linear gradients), and one or more RF coils 108 that are configured to transmit to RF signals to the patient's body and/or receive RF signals therefrom. The computer system 150 (embodiments of which are described in greater detail below) can store and implement MRI sequences protocols 152 and image reconstruction algorithms 154, as well as a variety of other software modules known in the technical field. The MRI sequence protocols 152 can be embodied as instructions that, when executed by the computer system 150, cause the computer system 150 to control the gradient coils 106 and/or RF coils 108 to apply a particular sequence of magnetic field gradients and/or RF pulses to the patient. The image reconstruction algorithms 154 can be embodied as instructions that, when executed by the computer system 150, cause the computer system 150 to reconstruct an image of the patient based on the RF signal received from the patient (e.g., by the RF coils 108) as caused by the MRI sequence applied thereto.

In one embodiment, the MRI sequence protocols 152 can include a STIR-UTE MRI sequence with a single TE that is configured to provide temperature-sensitive contrast of tissue between the temperatures of approximately −40° C. and approximately −8° C., thereby allowing tissue at lethal temperatures and tissue at non-lethal temperatures below 0° C. to be differentially visualized. In particular, the STIR-UTE MRI sequence can include (i) applying a short tau or $T_1$ inversion recovery, which is a series of pulses designed to suppress signals having a particular $T_1$, with an invention time (TI) given below and (ii) using UTE, which includes any echo time ≤500 msec. The inversion time required to null areas with a particular $T_1$ is given by:

$$T_I = -T_1 \ln\left(\frac{1 + e^{-T_{RO}/T_1}}{2}\right)$$

where $T_{RO} = T_I + NT_R$ $T_{Rel}$ is the total time per pass or the interval between successive inversion pulses and $T_{Rel}$ is the relaxation time allowed after data readout to allow for magnetization recovery. When $T_{RO} = 200$ ms is selected, the TI to null the frozen tissue at the critical temperature (−40° C.) is approximately 80 ms for 3 Tesla scanners. Tissues with longer $T_{1S}$ (~1200 ms), such as unfrozen soft-tissue, are suppressed as well, because the short $T_{RO}$ used ($T_{RO} \ll T_{1(soft-tissue)}$) does not allow for sufficient relaxation time between successive inversion pulses.

Figure 10:
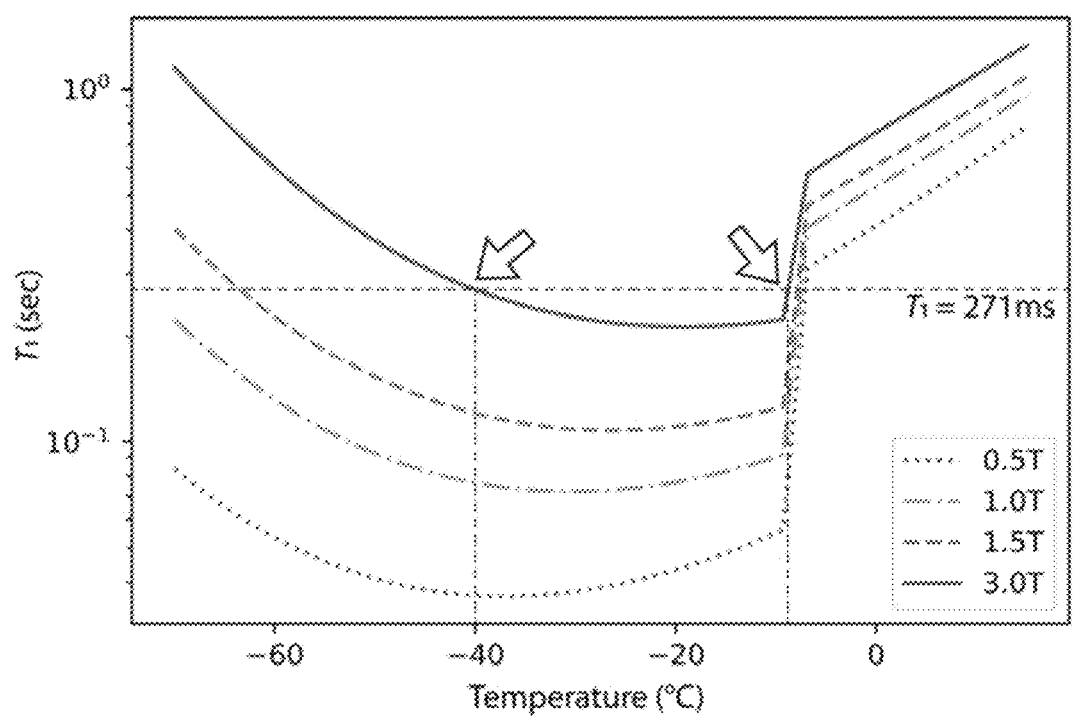
FIG. 10 is a graph illustrating the relationship between $T_1$ and temperature for various magnetic field strengths, in accordance with at least one aspect of the present disclosure.

This technique relies on the concept that the $T_1$ relaxation time of frozen tissue is strongly dependent on temperature and the Larmor frequency, as shown in FIG. 10. Notably, $T_1$ drops sharply as the temperature drops below −8° C., reaches a minimum at approximately −20° C. to −40° C., depending on the magnetic-field strength, and then gradually grows as temperatures further decrease. As a result, if the tissue $T_{1S}$ at the upper and lower temperature limits are known, the volume within this temperature range can be readily delineated with a STIR sequence that selectively suppresses signals with longer $T_{1S}$. The boundary temperatures are determined by the selected TI. In addition, since the TE of frozen tissues are extremely short (typically <200 μs), the STIR sequence is combined with a UTE readout in order to observe these tissue components. It should further be noted that the upper and lower temperature limits that can be visualized by the STIR-UTE MRI sequences described herein can be customized and are not solely limited to −8° C. and −40° C., respectively. The examples discussed herein where the upper limit is −8° C. and the lower limit is −40° C. are simply provided for illustrative purposes in the context of cryoablation procedures. In particular, the particular temperature range visualized by the STIR-UTE MRI sequence can be customized by adjusting the algorithm to target Tis for different upper and lower temperature limits.

In one embodiment, the image reconstruction algorithms 154 can further include an image processing package including three-dimensional models of ablated and insufficiently ablated tissue volumes at various times during cryoablation procedures. Accordingly, users and/or the computer system 150 could compare the visualized region to the provided three-dimensional models and provide an alert or other feedback to the user according to the comparison between the visualized region and the three-dimensional model(s). For example, if the visualized region corresponding to the temperature range targeted by the STIR-UTE MRI sequence corresponds to or matches a three-dimensional model of an insufficiently ablated volume, then the computer system 150 could provide an alert to the user and/or a recommendation to take various actions, such as lowering the temperature at one or more of the cryoprobes, inserting one or more additional cryoprobes, and so on.

Intraprocedural Use of STIR-UTE MRI Monitoring

Figure 2:
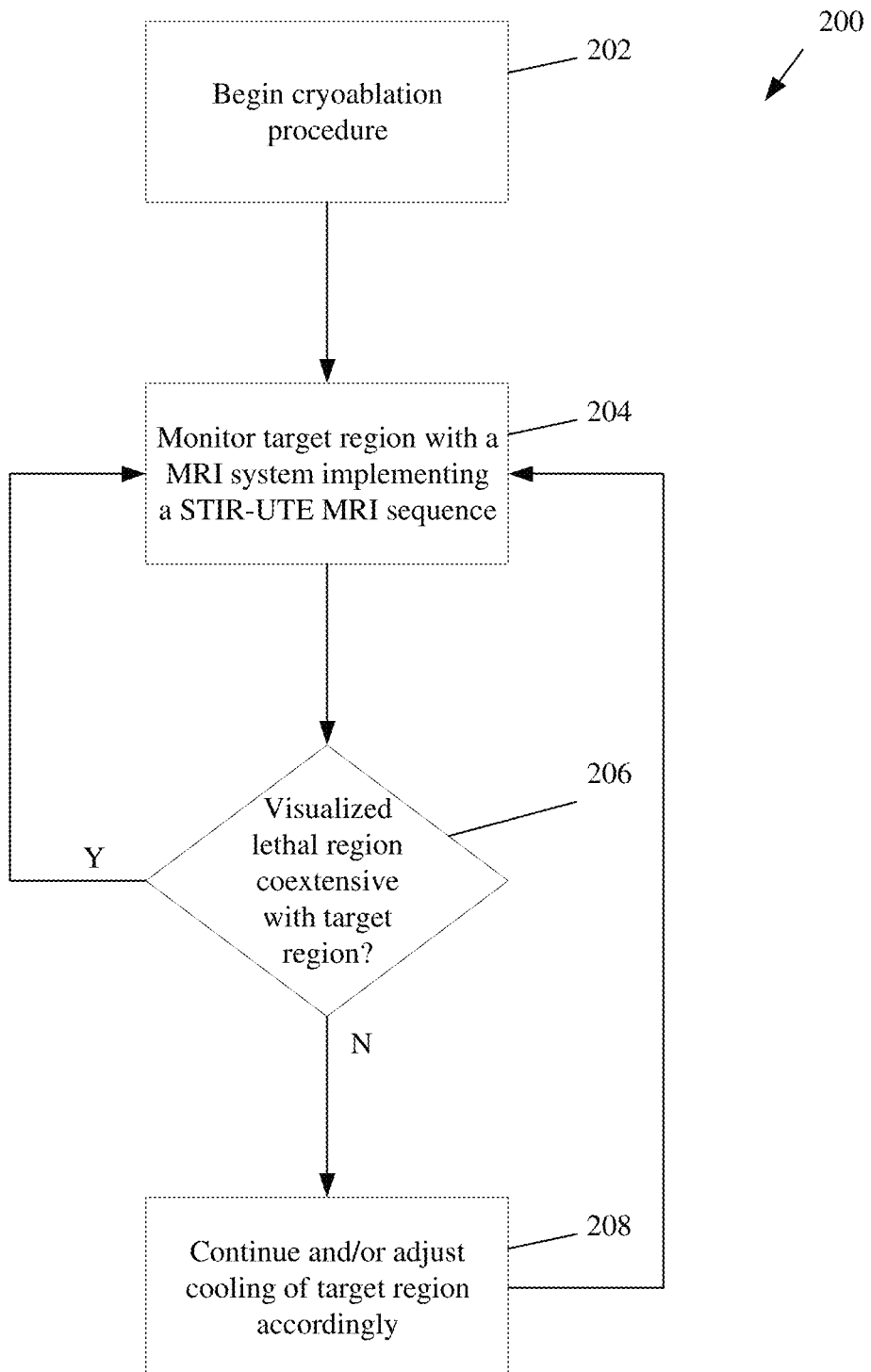
FIG. 2 is a flow diagram of a process for intraprocedurally monitoring a cryoablation procedure using STIR-UTE imaging, in accordance with at least one aspect of the present disclosure.

In various embodiments, the systems and methods described above for implementing STIR-UTE MRI sequences can be used for intraprocedural monitoring of different types of procedures, including cryoablation procedures, for example. As one illustrative example, FIG. 2 illustrates one such process 200 for intraprocedurally monitoring a cryoablation procedure using an MRI system implementing a STIR-UTE MRI sequence. However, it should be noted FIG. 2 is simply provided for illustrative purposes and the systems and methods described herein are not limited in application to only monitoring cryoablation procedures.

Initially, the medical team performing the process 200 can begin 202 the cryoablation procedure. As noted above, cryoablation procedures generally consist of inserting cryoprobes into a patient such that the tips of the cryoprobes at positioned at or adjacent to a target region (e.g., a tumor) and then cooling the tips (e.g., by circulating a cooled fluid through the cryoprobes) to freeze the target region. During the cryoablation procedure, the patient can be monitored 204 using an MRI system, such as the MRI system 100 described above that is configured to implement STIR-UTE MRI sequences for imaging frozen tissue. By monitoring the intraprocedural MR images, the medical team can determine 206 whether the visualized lethal region (i.e., the region between −40° C. and −8° C.) is coextensive with the target region. In other words, the medical team can determine 206 whether the lethal region is smaller than the target region, corresponds to the target region, or is larger than the target region. Examples of images obtained using STIR-UTE MRI sequences are described below in connection with FIGS. 4A-9.

If the visualized lethal region is coextensive with the target region, then the medical team can continue to monitor 204 the target region with the MRI system 100 during the course of the cryoablation procedure. If the visualized lethal region is not coextensive with the target region, then the medical team may continue and/or adjust 208 the cooling/freezing of the target region accordingly. For example, if the visualized lethal region is smaller than the target region (i.e., the target region is not being fully ablated by the procedure), the medical team could continue cooling the target region, lower the temperature at one or more of the cryoprobes, insert one or more additional cryoprobes, and/or take other actions to increase the size of the lethal region. As another example, if the visualized lethal region is larger than the target region, the medical team could cease cooling the target region and/or take other actions to decrease the size of the lethal region. As yet another example, if the visualized lethal region is an unexpected shape or configuration, the medical team could reposition the cryoprobes, add or remove cryoprobes, and/or take other actions to change the shape of the lethal region.

In one embodiment, the medical team can manually monitor the size and/or shape of the lethal region visualized by the STIR-UTE MRI sequence and adjust the cryoablation procedure accordingly. As discussed above, in another embodiment, a computer system 150 can additionally or alternatively be programmed to monitor the size and/or shape of the lethal region visualized by the STIR-UTE MRI sequence and automatically provide alerts and/or recommendations to the users (i.e., the medical team) accordingly.

Additional techniques can be used in combination with the aforementioned cryoablation techniques in order to enhance the rate of cell death. For example, one technique uses a dynamic spatial progression of the cold front induced by the cryoablation procedure over time, i.e., a spatial region that is at a particular temperature in the cryoablation procedure can be dynamically changed over time to enhance the rate of cell death. In particular, as the cold front induced by the cryoablation procedure advances through the tissue and freezes new tissue that it reaches, the frozen tissue expands in volume (e.g., by approximately 10%). As the frozen tissue expands in volume, the interstitial pressure applied to the tissue regions adjacent to the advancing cold front is increased. When tissues experience pressures that are beyond their mechanical/elastic limit, microfractures can be induced in the tissue regions. Microfractures can burst blood vessels, create fractures at interfaces between different tissues, and/or burst cell membranes, for example. This cell destruction mechanism is dependent on the rate of advance of the cold front because when the cold front moves more slowly through the tissue, the pressure increases can be propagated throughout adjacent tissue and dissipated more readily. Accordingly, the systems and methods described herein using STIR-UTE MRI sequences can be used to not only intraprocedurally monitor the size and/or shape of a defined temperate region, but also to intraprocedurally monitor the rate of change of the defined temperate region. In one embodiment, users and/or the computer system 150 could monitor the rate of change of the defined temperature region within the tissue to determine whether a desired rate of cell death is being induced at the boundary of the defined temperate region (i.e., at the cold front). In one embodiment, users could make adjustments to the cryoablation procedure based on the monitoring of the rate of change of the defined temperature region, such as by increasing the rate of cooling of the cryoprobe. In another embodiment, the computer system 150 could provide user alerts and/or recommendations based on the monitoring of the rate of change of the defined temperature region. In some embodiments, the lower bound of the temperature range for the STIR-UTE MRI sequence could be modified based on the rate of advancement of the spatial boundary of the region.

The STIR-UTE MRI techniques described above are primarily discussed in the context of monitoring cryoablation procedures; however, the techniques can also be used in the context of other procedures. For example, a STIR-UTE MRI sequence can be used to monitor tissue cryoprotection applications. In particular, a medical team could use a MRI system executing a STIR-UTE MRI sequence to monitor and guide a tissue cryoprotection procedure to ensure that the tissue is being cooled properly (e.g., for transplantation).

Computer System Architecture

FIG. 3 is an architecture diagram of an MRI system 100 that may be used in some embodiments. As noted above, the MRI system 100 can include a computer system 150 and an MRI machine 102. The computer system 150 may include one or more processors 802. Each processor 802 is connected to a communication infrastructure 806 (e.g., a communications bus, cross-over bar, or network). Computer system 150 may include a display interface 822 that forwards graphics, text, and other data from the communication infrastructure 806 (or from a frame buffer, not shown) for display on the display unit 824.

Computer system 150 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer system 150. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer system 150.

Computer system 150 may also include a communications interface 820. Communications interface 820 allows software and data to be transferred between computer system 150 and external devices. Examples of communications interface 820 may include a modem, Ethernet card, wireless network card, a Personal Computer Memory Card International Association (PCMCIA) slot and card, or the like. Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, a hard disk installed in hard disk drive 810, or removable storage unit 816. These computer program products provide software to computer system 150. Computer programs (also referred to as computer control logic) may be stored in main memory 804 and/or secondary memory 808. Computer programs may also be received via communications interface 820. Such computer programs, when executed by a processor, enable the computer system 150 to perform the features of the methods discussed herein. For example, main memory 804, secondary memory 808, or removable storage units 816 or 818 may be encoded with computer program code (instructions) for performing operations corresponding to various processes disclosed herein.

It is understood by those familiar with the art that the system described herein may be implemented in hardware, firmware, or software encoded (e.g., as instructions executable by a processor) on a non-transitory computer-readable storage medium.

EXAMPLES

Various examples and applications of the systems and methods implementing the STIR-UTE MRI sequences are provided below.

Figure 4C:
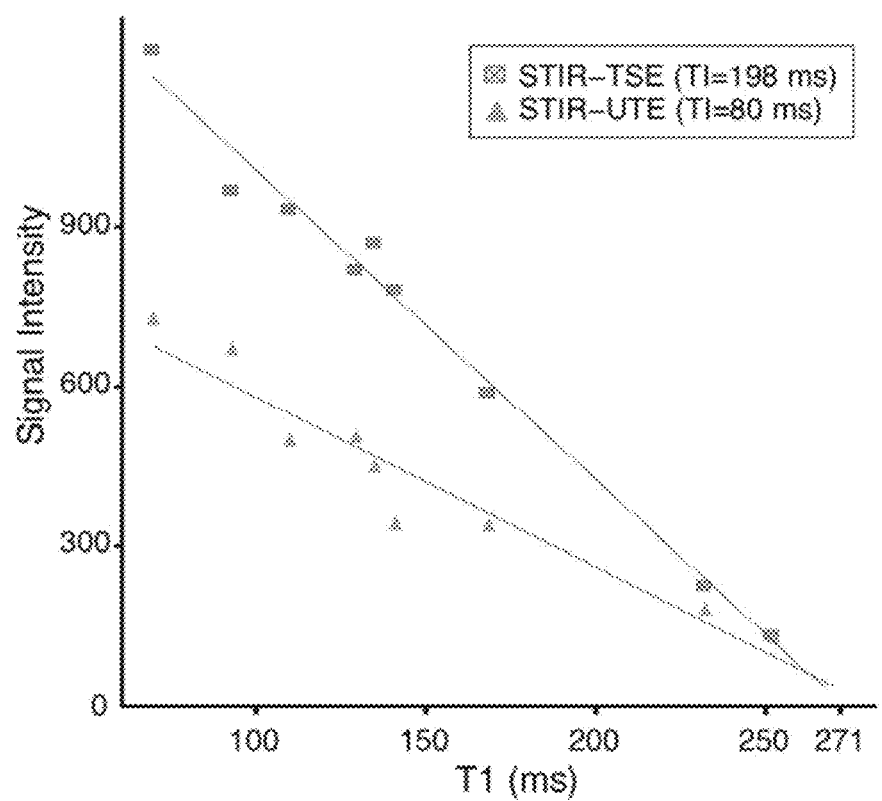
FIG. 4C is a graph plotting mean signal intensity relative to the $T_1$ relaxation times for the images shown in FIGS. 4A and 4B, in accordance with at least one aspect of the present disclosure.

Referring now to FIGS. 4A-C, there are shown a comparison of images of phantoms obtained using a conventional $T_2$-weighted TSE MRI sequence with a TI of 198 ms (FIG. 4A), images of the phantoms obtained using a STIR-UTE MRI sequence as described herein with a TI of 80 ms (FIG. 4B), and a graph plotting mean signal intensity relative to the $T_1$ relaxation times for the images obtained using the two MRI sequences. The $T_1$-mapping phantoms were nine vials containing gels with different concentrations. The $T_1$ relaxation times for the phantoms, which are shown below each of the images of the phantoms, were calculated by fitting the $T_1$ relaxation model to the STIR-TSE images obtained at multiple TIs. The plot indicates that the signal intensity would become zero on both STIR-TSE and STIR-UTE near the expected $T_1$ ($T_1$, −40° C.=271 ms), but that TSE cannot be used to image frozen tissue, since its TE is too long. The null point for TSE with a TI of 198 ms is expected to be T1=198/ln (2)=286 ms. Accordingly, FIGS. 4A-C demonstrate that the STIR-UTE MRI sequence described herein can be used to image frozen tissue, whereas conventional $T_2$-weighted TSE MRI sequences cannot.

Figure 5:
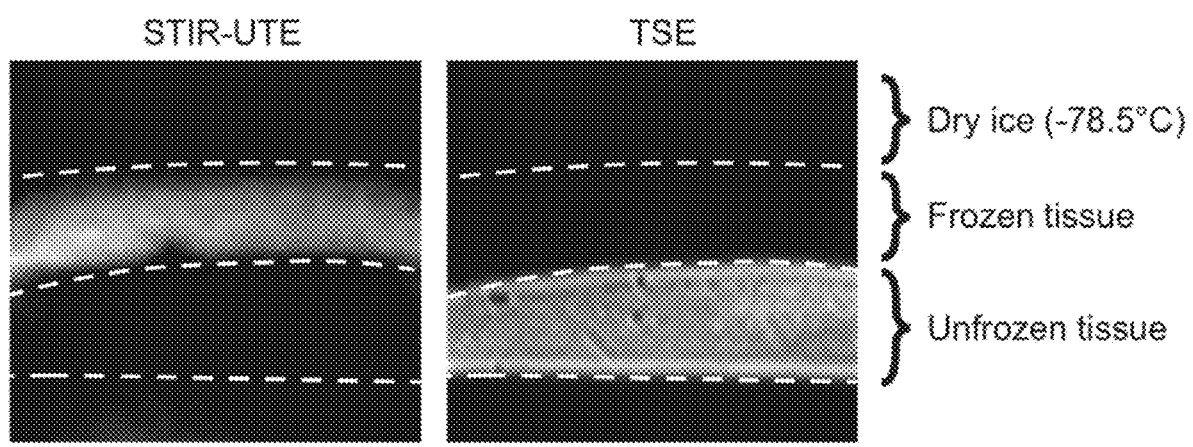
FIG. 5 is a comparison of images of a partially-frozen tissue sample obtained using STIR-UTE and TSE MRI sequences, in accordance with at least one aspect of the present disclosure.

Referring now to FIG. 5, there is shown a comparison of images of a tissue sample (swine muscle) obtained using a STIR-UTE MRI sequence (left) and a conventional TSE MRI sequence (right). The images in FIG. 5 were acquired approximately 40 minutes after dry ice was placed on top of the tissue sample, which created a layer of frozen tissue above the unfrozen layer. The relative positions of the dry ice, frozen tissue, and unfrozen tissue are illustrated in FIG. 5. As can be seen, the frozen layer is shown as a signal void on the TSE image, while the STIR-UTE image shows a band of hyperintensity between lower temperature and upper temperature boundaries (between approximately −40° C. and −8° C.) within the frozen tissue. In the STIR-UTE image, the signal was gradually suppressed near the dry ice corresponding to the decay slope below the lower temperature boundary (as shown in FIG. 6B). Further, the signal from the unfrozen layer was also suppressed in the STIR-UTE image. Accordingly, it can be seen that a STIR-UTE MRI sequence is especially adapted for visualizing tissue within this temperature range.

Figure 6A:
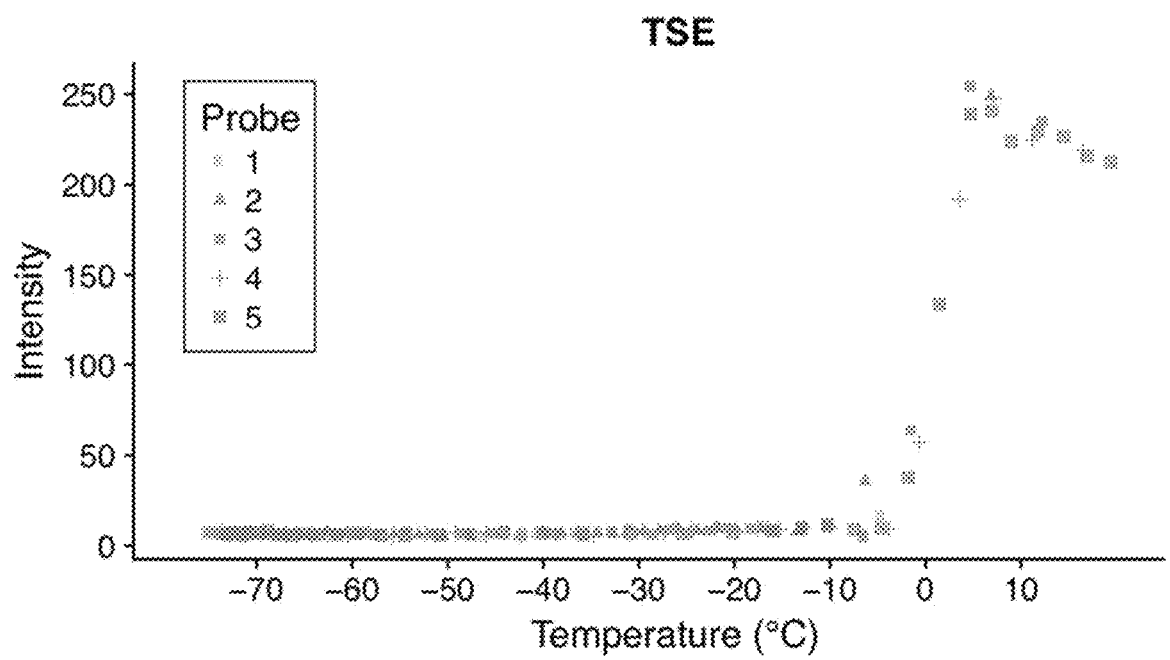
FIG. 6A is a graph of intensities of images of a tissue sample obtained using a conventional TSE MRI sequence relative to temperature, in accordance with at least one aspect of the present disclosure.
Figure 6B:
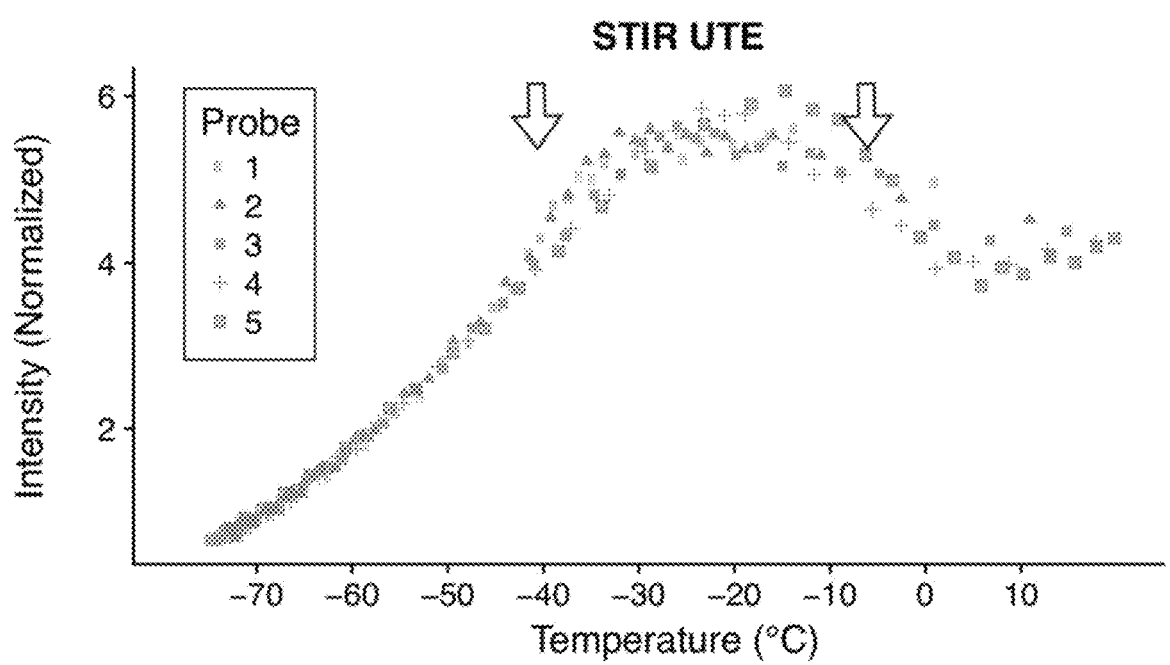
FIG. 6B is a graph of intensities of images of a tissue sample obtained using a STIR-UTE MRI sequence relative to temperature, in accordance with at least one aspect of the present disclosure.

Referring now to FIGS. 6A and 6B, there are shown graphs of intensities of images obtained using a conventional TSE MRI sequence (FIG. 6A) and a STIE-UTE MRI sequence (FIG. 6B) plotted relative to temperature. In this experiment, the temperature of the tissue sample was measured with thermocouples embedded into the tissue. The arrows indicate lower (−40° C.) and upper (−8° C.) temperatures where $T_1$ was expected to be 271 ms, which were the selected signal-nulling temperatures. Note that image intensities below and above these temperatures were attenuated. Accordingly, it can be seen that a STIR-UTE MRI sequence generates image intensities that peak between the selected lower (−40° C.) and upper (−8° C.) temperatures.

Figure 7A:
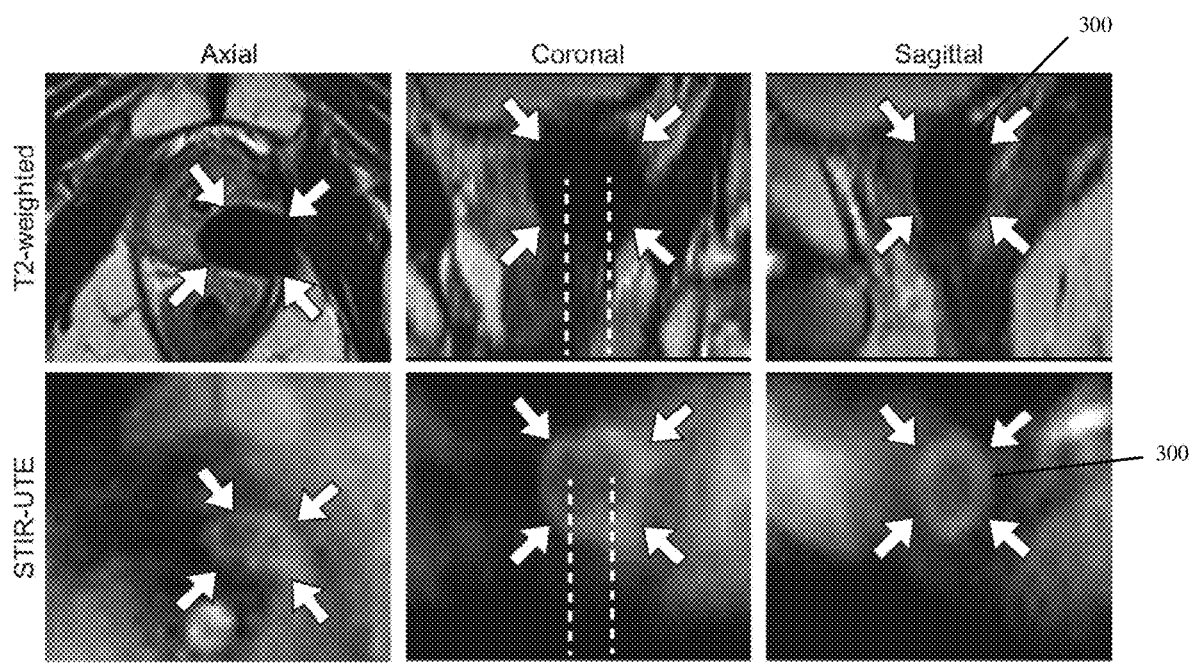
FIG. 7A is a set of images of a prostate being treated during a cryoablation procedure that were obtained using conventional $T_2$-weighted TSE and STIR-UTE MRI sequences, in accordance with at least one aspect of the present disclosure.
Figure 7B:
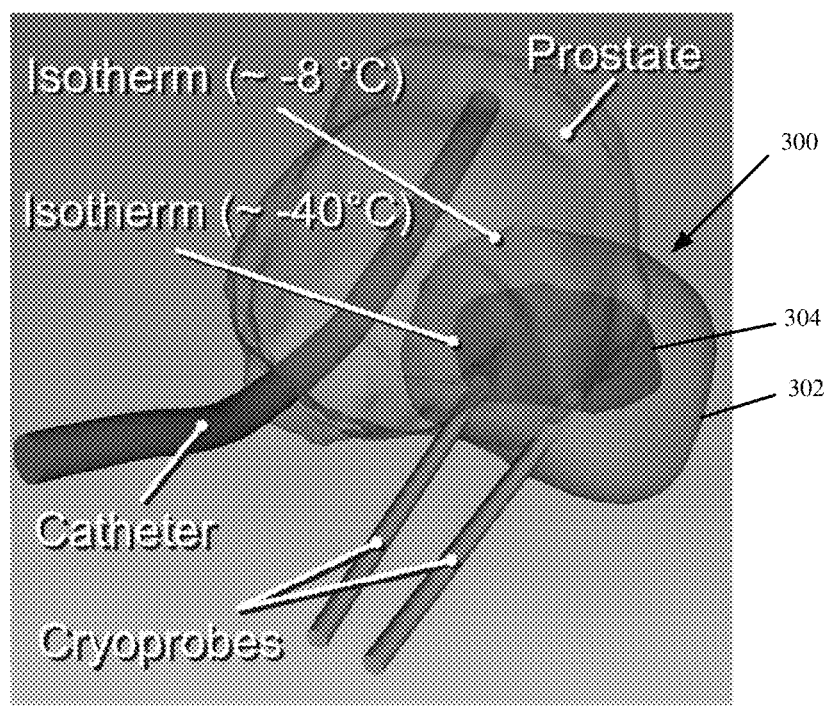
FIG. 7B is a three-dimensional rendering of the target region reconstructed from the STIR-UTE images in FIG. 7A, in accordance with at least one aspect of the present disclosure.

Referring now to FIGS. 7A and 7B, there are shown axial, coronal, and sagittal images of a prostate being treated during a cryoablation procedure that were obtained using conventional $T_2$-weighted TSE and STIR-UTE MRI sequences (FIG. 7A) and a three-dimensional rendering of the target region reconstructed from the STIR-UTE images. The images shown in FIG. 7A were acquired in the axial plane (left column) and reformatted along the coronal (middle column) and sagittal planes (right column). In this procedure, two cryoprobes were placed in parallel to the coronal plane (as indicated by the dotted lines). As can be seen by comparing the two sets of images, the TSE images show the target region 300 as a void or completely dark (indicating that the region that is at 0° C. or lower, i.e., the "ice ball"), whereas the STIR-UTE images show the target region 300 as a doughnut-shaped hyperintense area. The doughnut shaped region approximately represents the −8° C. (outer edge) and −40° C. (inner edge) isotherms. As further shown in the three-dimensional rendering of FIG. 7B, the STIR-UTE MRI sequence can be used to differentiate between the −8° C. isotherm 302 (which corresponds to a volume that is at or less than −8° C.) and the −40° C. isotherm 304 (which corresponds to a volume that is at or less than −40° C.). Therefore, STIR-UTE images can be used to differentiate between regions that are at a lethal temperature and regions that are at a non-lethal frozen temperature, which is a clear improvement over the prior art. FIG. 7B shows these volumes reconstructed from the STIR-UTE images in FIG. 7A, along with models of the prostate gland, the cryoprobes, and the urethral warming catheter used in the cryoablation procedure. The coronal STIR-UTE image and the 3D renderings clearly demonstrate the synergistic effect that is obtained when the ice balls created by each of the cryoprobes fuse together, thus providing a larger low-temperature region.

Figure 8A:
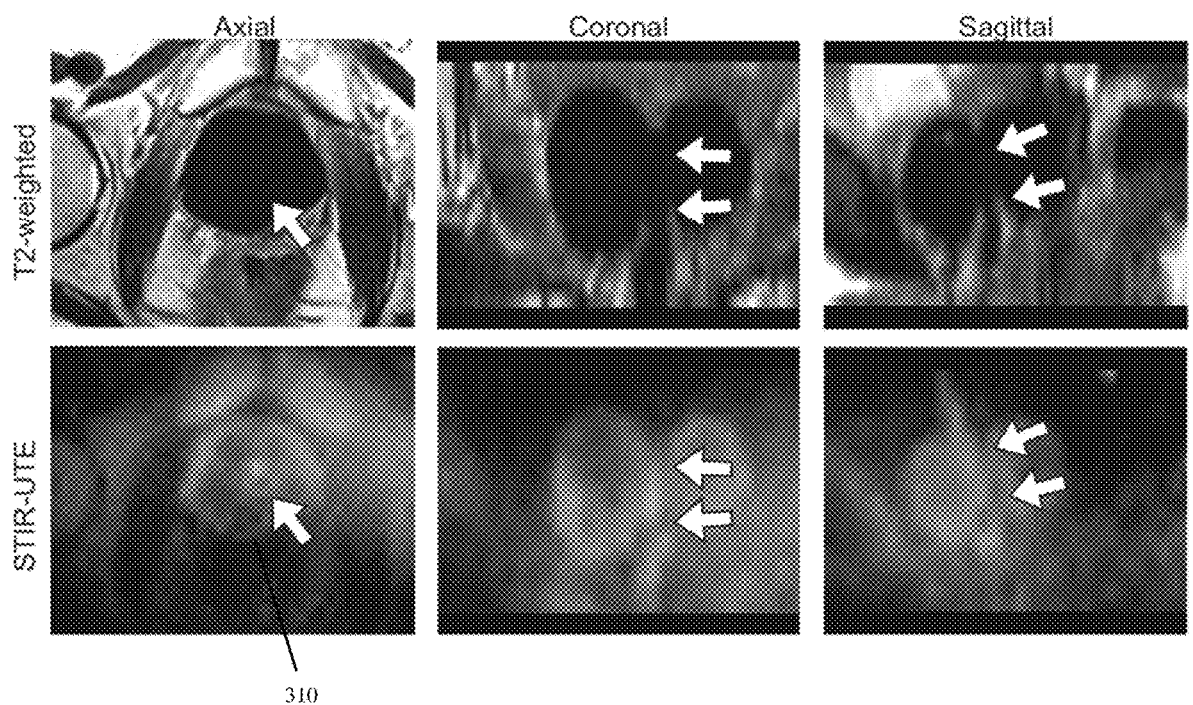
FIG. 8A is a set of images of a prostate being treated during a cryoablation procedure that were obtained using conventional $T_2$-weighted TSE and STIR-UTE MRI sequences, in accordance with at least one aspect of the present disclosure.
Figure 8B:
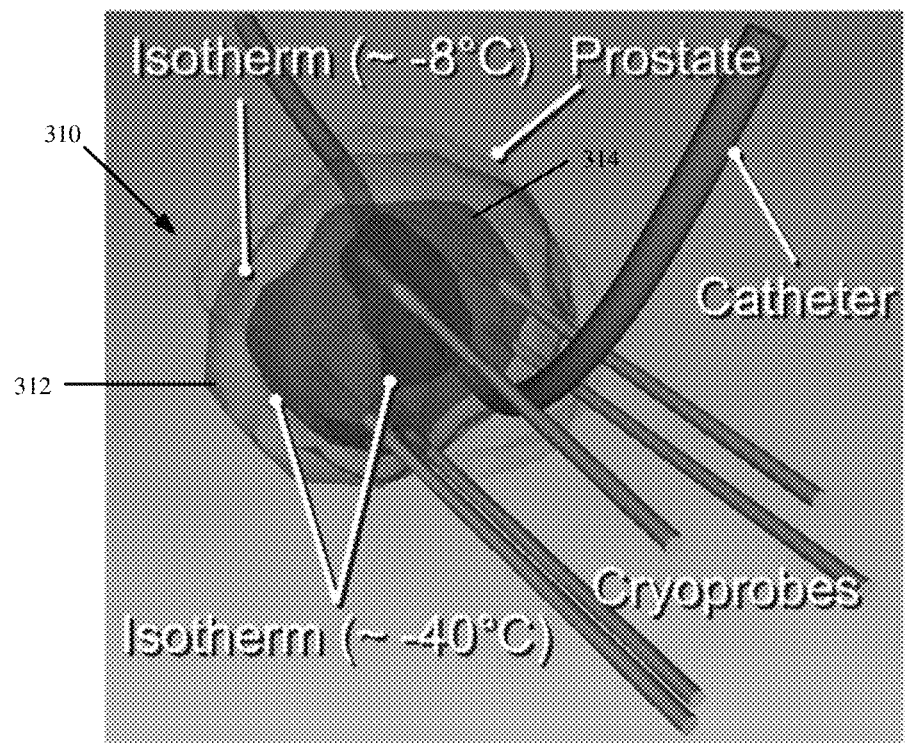
FIG. 8B is a three-dimensional rendering of the target region reconstructed from the STIR-UTE images in FIG. 8A, in accordance with at least one aspect of the present disclosure.

Referring now to FIGS. 8A and 8B, there are shown axial, coronal, and sagittal images of a prostate being treated during another cryoablation procedure that were obtained using conventional $T_2$-weighted TSE and STIR-UTE MRI sequences (FIG. 8A) and a three-dimensional rendering of the target region reconstructed from the STIR-UTE images (FIG. 8B). In this particular procedure, a large portion of the prostate gland involving the urethra was ablated with five cryoablation probes, resulting in a large signal void on the $T_2$-weighted TSE images. Further, the STIR-UTE images show a hypointense region around the urethra (indicated by the white arrows in FIG. 8A), indicating a higher tissue temperature, which is because of the catheter with circulating warm water that was placed within the urethra to protect it from cryoinjury. Similarly to the example shown in FIGS. 7A and 7B, the TSE images show the target region 310 as a void or completely dark (indicating that the region that is at 0° C. or lower, i.e., the "ice ball"), whereas the STIR-UTE images show the target region 310 as a doughnut-shaped hyperintense area. As further shown in the three-dimensional rendering of FIG. 8B, the STIR-UTE MRI sequence can be used to differentiate between the −8° C. isotherm 312 (which corresponds to a volume that is at or less than −8° C.) and the −40° C. isotherm 314 (which corresponds to a volume that is at or less than −40° C.). Therefore, STIR-UTE images can be used to differentiate between regions that are at a lethal temperature and regions that are at a non-lethal frozen temperature, which is a clear improvement over the prior art.

Figure 9:
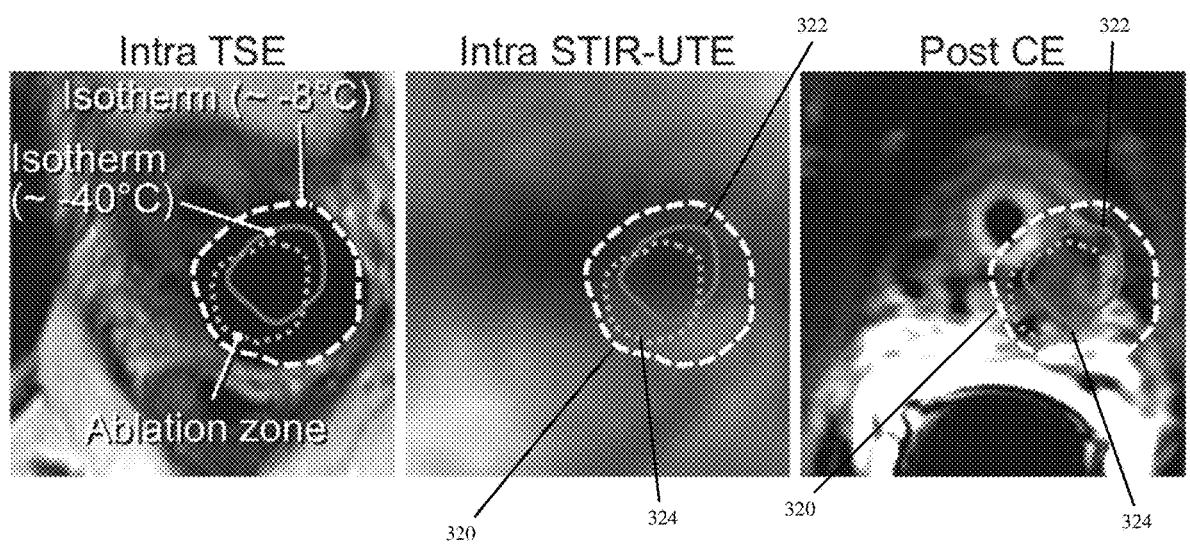
FIG. 9 is a set of images including an intraprocedural TSE image (left), an intraprocedural STIR-UTE image (middle), and a postprocedural contrast-enhanced (CE) MRI at corresponding slice locations of a prostate treated by a cryoablation procedure, in accordance with at least one aspect of the present disclosure.

Referring now to FIG. 9, there is shown a comparison between an intraprocedural TSE image (left), an intraprocedural STIR-UTE image (middle), and a postprocedural contrast-enhanced (CE) MR image (right) at corresponding slice locations of a prostate treated by a cryoablation procedure. The postprocedural CE MRI was acquired in a separate session and was aligned to the intraprocedural images manually. In each of the images, the −8° C. isotherm 320, −40° C. isotherm 322, and the ablation zone 324 are indicated thereon. The ablation zone 324 was estimated from the unenhanced area on the postprocedural CE image. The volume of the ablation zone 324 was 6.20 cc, while the maximum volumes within the boundary near the −40° C. isotherm 322 on the STIR-UTE was 5.08 cc. As can be seen in the images, the intraprocedural TSE image shows the entire area within the −8° C. isotherm 320 as a void, whereas the STIR-UTE image shows a contrast between the −8° C. isotherm 320 and the −40° C. isotherm 322. Further, the images indicate that the visualized −40° C. isotherm 322 closely corresponds to the postprocedural estimated ablation zone 324.

In summary, the present disclosure describes systems and methods for predicting the lethal ablation zone using a STIR-UTE MRI. Further, the examples described herein show that STIR-UTE images can successfully delineate the area in a defined temperature range (e.g., between −40° C. and −8° C.), i.e., isotherms, in frozen tissue. In particular, STIR-UTE images obtained using the systems and methods describe herein provide positive contrast in the frozen tissue approximately between −8° C. and −40° C. isotherms. While the estimated lethal temperatures may vary between −20° C. to −40° C., this method permits adjusting the boundary temperatures in which hyperintense contrasts are obtained by changing the selected $T_1$ of the STIR-UTE sequence. Accordingly, the systems and methods described herein provide an alternative approach to conventional MR-based cryoablation monitoring. Further, the systems and methods described herein are able to directly visualize frozen tissue that is likely above the cell death temperature, which is a simpler way to confirm ablation margins (without the need for any post-processing) relative to other techniques that require a quantitative measurement of R2* or intensity changes and a subsequent temperature conversion calculation based on prior calibrations.

Additional description regarding temperature-sensitive frozen tissue imaging can be found in "Temperature-Sensitive Frozen-Tissue Imaging for Cryoablation Monitoring Using STIR-UTE MRI" by Tokuda, Junichi et al., Investigative radiology vol. 55, 5 (2020), which is hereby incorporated by reference herein in its entirety.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An MRI system for imaging a patient, the MRI system comprising:
   an MRI machine; and
   a computer system coupled to the MRI machine, the computer system comprising:
      a processor, and
      a memory coupled to the processor, the memory storing instructions that, when executed by the processor, cause the computer system to:
         control the MRI machine to apply an MRI sequence comprising a short tau inversion recovery sequence and an ultrashort echo time, wherein the short tau inversion recovery sequence utilizes a $T_1$ value such that an image signal is attenuated from tissue below a lower temperature and above an upper temperature,
         reconstruct an image of the patient in response to the MRI sequence, the image visualizing a region corresponding to the upper temperature and the lower temperature, wherein the region corresponding to the upper temperature and the lower temperature includes a first region and a second region, the first region corresponding to a first temperature range and the second region corresponding to a second temperature range, temperatures of the first temperature range being lower than temperatures of the second temperature range,
         compare the region corresponding to the upper temperature and the lower temperature to a target region to determine if the region corresponding to the upper temperature and the lower temperature is coextensive with the target region,
         differentiate the first region and the second region relative to the target region,
         monitor a rate of change of the region corresponding to the upper temperature and the lower temperature to determine a rate of cell death at a boundary of the region corresponding to the upper temperature and the lower temperature,
         provide a recommendation for adjusting a rate of cooling of a cryoprobe based on the rate of change of the region corresponding to the upper temperature and the lower temperature, and
         provide a recommendation for modifying the lower temperature based on the rate of change of the region corresponding to the upper temperature and the lower temperature.

2. The MRI system of claim 1, wherein the upper temperature is −8° C. and the lower temperature is −40° C.

3. The MRI system of claim 1, wherein the upper temperature is non-lethal to cells and the lower temperature is lethal to cells.

4. The MRI system of claim 1, wherein the memory further stores instructions that, when executed by the processor, cause the computer system to:
   compare the region corresponding to the upper temperature and the lower temperature in the image to a three-dimensional model of an ablated tissue volume or a three-dimensional model of an insufficiently ablated tissue volume, and
   provide an alert according to the comparison.

5. The MRI system of claim 1, wherein the region corresponding to the upper temperature and the lower temperature corresponds to a void in a $T_2$-weighted MRI.

6. A method for imaging a patient, the method comprising:
   controlling, via a computer system, an MRI machine to apply an MRI sequence comprising a short tau inversion recovery sequence and an ultrashort echo time, wherein the short tau inversion recovery sequence utilizes a $T_1$ value such that an image signal is attenuated from tissue below a lower temperature and above an upper temperature;
   reconstructing, via the computer system, an image of the patient in response to the MRI sequence, the image visualizing a region corresponding to the upper temperature and the lower temperature, wherein the region corresponding to the upper temperature and the lower temperature includes a first region and a second region, the first region corresponding to a first temperature range and the second region corresponding to a second temperature range, temperatures of the first temperature range being lower than temperatures of the second temperature range;

comparing the region corresponding to the upper temperature and the lower temperature to a target region to determine if the region corresponding to the upper temperature and the lower temperature is coextensive with the target region;

differentiating the first region and the second region relative to the target region;

monitoring a rate of change of the region corresponding to the upper temperature and the lower temperature to determine a rate of cell death at a boundary of the region corresponding to the upper temperature and the lower temperature;

providing a recommendation for adjusting a rate of cooling of a cryoprobe based on the rate of change of the region corresponding to the upper temperature and the lower temperature; and providing a recommendation for modifying the lower temperature based on the rate of change of the region corresponding to the upper temperature and the lower temperature.

7. The method of claim 6, wherein the upper temperature is −8° C. and the lower temperature is −40° C.

8. The method of claim 6, wherein the upper temperature is non-lethal to cells and the lower temperature is lethal to cells.

9. The method of claim 6, further comprising:

comparing, via the computer system, the region corresponding to the upper temperature and the lower temperature in the image to a three-dimensional model of an ablated tissue volume or a three-dimensional model of an insufficiently ablated tissue volume, and providing, via the computer system, an alert according to the comparison.

10. The method of claim 6, wherein the region corresponding to the upper temperature and the lower temperature corresponds to a void in a $T_2$-weighted MRI.

11. A method for monitoring a patient during a cryoablation procedure, the method comprising:

visualizing, via an MRI system configured to apply an MRI sequence comprising a short tau inversion recovery sequence and an ultrashort echo time, wherein the short tau inversion recovery sequence utilizes a $T_1$ value such that an image signal is attenuated from tissue below a lower temperature and above an upper temperature, a region corresponding to the upper temperature and the lower temperature, the region corresponding to the upper temperature and the lower temperature including a first region and a second region relative to a target region, the first region corresponding to a first temperature range and the second region corresponding to a second temperature range, temperatures of the first temperature range being lower than temperatures of the second temperature range;

determining whether the region corresponding to the upper temperature and the lower temperature is coextensive with the target region;

providing feedback for the cryoablation procedure according to the determination;

differentiating the first region and the second region relative to the target region;

monitoring a rate of change of the region corresponding to the upper temperature and the lower temperature to determine a rate of cell death at a boundary of the region corresponding to the upper temperature and the lower temperature;

providing a recommendation for adjusting a rate of cooling of one or more cryoprobes adjacent to the target region based on the rate of change of the region corresponding to the upper temperature and the lower temperature; and providing a recommendation for modifying the lower temperature based on the rate of change of the region corresponding to the upper temperature and the lower temperature.

12. The method of claim 11, wherein the upper temperature is −8° C. and the lower temperature is −40° C.

13. The method of claim 11, wherein the upper temperature is non-lethal to cells and the lower temperature is lethal to cells.

14. The method of claim 11, wherein the target region comprises a tumor.

15. The method of claim 11, wherein providing the feedback comprises recommending at least one of continuing to cool the target region, lowering the temperature at the one or more cryoprobes adjacent to the target region, or inserting one or more additional cryoprobes adjacent to the target region.

16. The method of claim 11, wherein the region corresponding to the upper temperature and the lower temperature corresponds to a void in a $T_2$-weighted MRI.

* * * * *